United States Patent
Ivanova et al.

(10) Patent No.: US 9,073,837 B2
(45) Date of Patent: Jul. 7, 2015

(54) DEHYDRATION OF METHANOL TO DIMETHYL ETHER USING CATALYSTS BASED ON A ZEOLITE SUPPORTED ON SILICON CARBIDE

(75) Inventors: Svetlana Ivanova, Strasbourg (FR); Estelle Vanhaecke, Strasbourg (FR); Suzanne Libs, Schiltigheim (FR); Benoit Louis, Eckbolsheim (FR); Cuong Pham-Huu, Saverne (FR); Marc Jacques Marie Ledoux, Strasbourg (FR)

(73) Assignees: CENTRE NATIONAL DE LA RECHERCHE SCIENTIFIQUE (C.N.R.S.), Paris (FR); UNIVERSITE LOUIS PASTEUR, Strasbourg (FR)

( * ) Notice: Subject to any disclaimer, the term of this patent is extended or adjusted under 35 U.S.C. 154(b) by 792 days.

(21) Appl. No.: 12/518,196

(22) PCT Filed: Dec. 7, 2007

(86) PCT No.: PCT/FR2007/002017
§ 371 (c)(1),
(2), (4) Date: Sep. 16, 2009

(87) PCT Pub. No.: WO2008/090268
PCT Pub. Date: Jul. 31, 2008

(65) Prior Publication Data
US 2010/0010272 A1 Jan. 14, 2010

(30) Foreign Application Priority Data
Dec. 8, 2006 (FR) .................................... 06 10743

(51) Int. Cl.
*C07C 41/09* (2006.01)
(52) U.S. Cl.
CPC ..................................... *C07C 41/09* (2013.01)
(58) Field of Classification Search
CPC ........................................................ C07C 41/09

USPC .......................................................... 568/698
See application file for complete search history.

(56) References Cited

U.S. PATENT DOCUMENTS

| 4,177,167 | A | | 12/1979 | Manara et al. | |
|---|---|---|---|---|---|
| 4,560,807 | A | | 12/1985 | Murai et al. | |
| 5,316,627 | A | * | 5/1994 | Hammer | 203/34 |
| 7,179,764 | B2 | | 2/2007 | Basso et al. | |
| 2003/0162649 | A1 | * | 8/2003 | Basso et al. | 502/64 |

FOREIGN PATENT DOCUMENTS

| EP | 0 270 852 | 6/1988 |
|---|---|---|
| GB | 403 402 | 11/1933 |
| GB | 1 398 696 | 6/1975 |
| GB | 2 099 327 | 12/1982 |
| WO | 03/059509 | 7/2003 |
| WO | 2004/074228 | 9/2004 |

OTHER PUBLICATIONS

Ki-Won Jun et al., "Highly Water-Enhanced H-ZSm-5 Catalysts for Dehydration of Methanol to Dimethyl Ether", Bull. Korean Chem. Soc. 2003, vol. 24, No. 1, pp. 106-108.
Takashi Ogawa et al., "Direct Dimethyl Ether Synthesis", Journal of Natural Gas Chemistry 12(2003), pp. 219-227.
Troy Semelsberger et al., "Thermodynamic Equilibrium Calculations of Dimethyl Ether Steam Reforming and Dimethyl Ether Hydrolysis", Journal of Power Sources ISSN 0378-7753, vol. 152, 2005, pp. 87-96 (Abstract only).
International Search Report dated Jun. 13, 2008, from corresponding PCT application.

* cited by examiner

*Primary Examiner* — Rosalynd Keys
(74) *Attorney, Agent, or Firm* — Young & Thompson (57) ABSTRACT

A process for the preparation of dimethyl ether by catalytic dehydration of methanol, in which there is used a catalyst based on a zeolite immobilized on a silicon carbide support, for example a zeolite of type ZSM-5 supported on silicon carbide extrudates or on a silicon carbide cellular foam.

19 Claims, 3 Drawing Sheets

DEHYDRATION OF METHANOL TO DIMETHYL ETHER USING CATALYSTS BASED ON A ZEOLITE SUPPORTED ON SILICON CARBIDE

FIELD OF THE INVENTION

The present invention relates to the field of the conversion of methanol into dimethyl ether. More precisely, the invention relates to an improved, particularly efficient method for converting methanol into dimethyl ether, which method is found to be suitable especially for the large-scale production of dimethyl ether.

BACKGROUND OF THE INVENTION

Dimethyl ether, which has the formula $CH_3$—O—$CH_3$, is a compound whose industrial synthesis has many applications.

Dimethyl ether can especially be used as a precursor for the synthesis of various compounds of interest, such as low molecular weight olefins, methyl acetate or dimethyl sulfate. It can also be used as such, for example as a propellant.

More specifically, dimethyl ether has been proposed as an alternative fuel to advantageously replace petroleum derivatives. It is a readily liquefiable gas (its boiling point is −25° C.) which has a cetane index comparable to that of diesel. In addition, dimethyl ether has the advantage of being much less polluting than petroleum derivatives, especially in terms of sulfur oxide, nitrogen oxide and soot emission, which makes it more compatible with recent developments in legislation relating to exhaust gases. For further details regarding the advantages of using dimethyl ether as an alternative fuel, reference may be made especially to the article by Semelsberger et al. in *Journal of Power Resources* Vol. 152(1), pp. 87-89 (2005).

At the present time, dimethyl ether is already being used in the domestic fuel sector to replace liquefied gases obtained from petroleum (butane and propane), and it is being considered as a fuel for the large-scale production of electricity, especially in India where, on its own, it should provide half the electricity produced in 2010.

A conventional production technique consists in synthesising dimethyl ether from a mixture of CO and $H_2$ (so-called "synthesis gas" mixture), which is reacted with a suitable catalyst (generally based on metallic oxide), for example according to the methods described by T. Ogawa et al. in *Journal of Natural Gas Chemistry* Vol. 12, pp. 219-227 (2003) or alternatively in documents GB 1 398 696, U.S. Pat. No. 4,177,167, GB 2 099 327 or GB 2 093 365.

Another technique for synthesising dimethyl ether, which has been developed more recently, consists in preparing that compound by dehydrating methanol on an acidic catalyst according to the following reaction:

$$2CH_3OH \rightarrow CH_3—O—CH_3 + H_2O$$

This reaction has been described especially by K. W. Jun et al. in *Bulletin Korean Chemical Society* Vol. 24, p. 106 (2003).

The above-mentioned methanol dehydration reaction usually employs solid catalysts based on gamma aluminium or modified gamma aluminium, of the type described, for example, in documents U.S. Pat. No. 4,560,807, EP 270 852 or GB 403 402. Such catalysts have a disadvantage, namely that, given their hydrophilic nature, they are deactivated in the presence of water, which prevents their use especially for the conversion of methanol obtained from biomass unless laborious and costly methanol pretreatment processes are carried out.

In order to remedy the disadvantages encountered with catalysts of the gamma aluminium type, more specific catalyst systems have been proposed.

In WO 04/74228 there is described a dual catalyst system which makes use of a hydrophilic acidic catalyst, which allows to convert methanol into dimethyl ether, coupled with a hydrophobic acidic catalyst, which ensures that the methanol is maintained in a state of dehydration. Although this system exhibits good synthesis yields, it is found to be rather difficult to carry out.

In order to catalyse the methanol dehydration reaction the use of zeolites has also been considered, especially MFI-type zeolites, for example zeolite ZSM-5, which are relatively stable in the presence of water and the acidity of which can be modified, especially by impregnating them with a solution of sodium salts, which allows relatively good yields to be obtained.

Nevertheless, in connection with these various advantages, the use of zeolites of the type of the zeolite ZSM-5 is found to be not entirely satisfactory in practice, in particular when it is desired to use the dehydration reaction on a large scale.

In fact, it should be emphasised that such catalysts have a major disadvantage, namely that they are not stable over time. More precisely, it is found that, when catalysts constituted of zeolite of the ZSM-5 type are used to carry out the conversion reaction of methanol to dimethyl ether, a very rapid loss of activity of the catalyst is generally observed, which manifests itself in concrete terms in a very marked reduction in the methanol conversion over time, the loss of activity generally being observed after very short reaction times of the order of several hours at most, typically after from 2 to 6 hours of reaction.

It seems that the loss of catalytic activity observed when catalysts constituted of zeolites such as ZSM-5 are used can be explained at least partly by a so-called coking phenomenon, namely the gradual deposition of carbon within the structure of the zeolite. Also to be taken into account are a possible alteration of the zeolite structure by the water vapour formed during the conversion reaction of methanol to dimethyl ether, as well as the potential influence of the regeneration of the structure of the catalyst in the air. Moreover, the conversion reaction is exothermal, which is liable to form hot spots on the catalyst which are capable of promoting the above-mentioned phenomena.

Furthermore, catalysts made of zeolites such as ZSM-5 have another disadvantage: they are in most cases in the form of powders, which are relatively difficult to use and lead especially to considerable losses of potential within the reactors, preventing their use on an industrial scale. In order to avoid that problem, it has been proposed to form the zeolite powders into macroscopic solids, especially by extrusion in the presence of inorganic binders of the silicon oxide or aluminium oxide type. However, such a solution is found to be unsatisfactory especially insofar as the binding agents used render part of the zeolite inaccessible, and they are additionally liable to induce undesirable secondary reactions.

SUMMARY OF THE INVENTION

An object of the present invention is to provide a novel method for synthesising dimethyl ether by dehydration of methanol, which method being suitable for the large-scale production of dimethyl ether and overcomes the above-mentioned problems, especially in terms of instability of the catalyst.

DETAILED DESCRIPTION OF THE INVENTION

To this end, an object of the invention is to a process for the preparation of dimethyl ether by catalytic dehydration of methanol, wherein the used as catalyst is a zeolite immobilised on a silicon carbide (SiC) support, said silicon carbide support preferably having a specific surface area greater than 2 m$^2$/g and more preferably greater than or equal to 5 m$^2$/g.

The zeolite used as the catalyst within the scope of the present invention may be chosen from any zeolite suitable for catalysing the conversion reaction of methanol to dimethyl ether.

The term "zeolite" is here understood as a material having the specific three-dimensional structure of zeolites of the aluminosilicate type, the skeleton of which is constituted of a chain of tetrahedrons TO$_4$, where T represents a silicon or aluminium atom. Most frequently, the zeolite used according to the invention is an aluminosilicate but, in the sense of the present description, the term "zeolite" also encompasses aluminosilicates wherein all or some of the silicon and aluminium atoms have been replaced by other elements. For example, silicon can be replaced by other tetravalent elements, for example tin, germanium and/or phosphorus, and aluminium can be replaced by other trivalent elements, for example boron, titanium, gallium and/or indium. Accordingly, in the sense in which it is used herein, the expression "zeolite" especially includes zeolites selected from the metallosilicates (for example gallosilicates, chromosilicates, borosilicates, ferrisilicates and titanosilicates), the metalloaluminophosphates (MeAPO), the aluminophosphates (ALPO) and the metallophosphates.

The zeolite used according to the invention can include zeolites of the structural type MFI, AEL, BEA, CHA, CLO, ERI, EUO, FAU, FER, HEU, LTA, LTL, MAZ, MEI, MEL, MOR, MTT, MTW, MWW, OFF, PHI, SOD and/or TON, as described in *Atlas Of Zeolite Structure Types* by W. M. Meier and D. H. Olson, Butterworth-Heinemann, 3rd edition, 1992.

Advantageously, the zeolite used within the scope of the invention is an MFI-type zeolite. A "MFI-type zeolite" is here understood as being a zeolite exhibiting the MFI structure as described in *Atlas Of Zeolite Structure Types* mentioned in the preceding paragraph, that zeolite preferably a zeolite which is substantially the MFI structure.

In addition, the zeolite used may advantageously be a silica based on an aluminosilicate wherein the molar ratio Si/Al is advantageously from 20 to 100, preferably from 40 to 80.

Particularly preferably, the zeolite used according to the invention is a ZSM-5 zeolite.

Within the scope of the present invention, the zeolites used are employed in the state supported on a specific silicon carbide support which preferably has a specific surface area of at least 2 m$^2$/g, more preferably greater than or equal to 5 m$^2$/g, for example greater than 10 m$^2$/g.

Within the scope of the present description, the term "silicon carbide support" is understood as being a solid support which comprises SiC as the major constituent and which is capable of immobilising a layer of zeolite on its surface.

The silicon carbide support present in the catalysts of the invention is generally constituted quasi-substantially (or even exclusively) of SiC. However, the presence of species other than SiC, especially of unavoidable impurities, is not ruled out. In that case, however, it is generally preferred for the SiC to be present in the support in an amount of at least 80% by mass, more preferably at least 85% by mass, and more advantageously at least 90% by mass. According to a particularly suitable embodiment of the invention, the support comprises at least 95% by mass SiC, preferably at least 98% by mass, more advantageously at least 99% by mass.

The used silicon carbide support is most frequently in the form of macroscopic solid objects having dimensions typically greater than 1 mm. Accordingly, they can be grains, extrudates, rods, monoliths, tubes, trilobes or rings, or alternatively foams, especially rigid cellular foams.

In the scope of the work which led to the present invention, the inventors have evidenced that the immobilisation of zeolites on a specific silicon carbide support results in a wholly unexpected effect, namely a very marked stabilisation of the catalyst in the conversion reaction of methanol to dimethyl ether, more particularly when the silicon carbide support has a high specific surface area, for example greater than or equal to 5 m$^2$/g.

More precisely, while the activity of non-supported zeolites decreases rapidly over time, it is found that the use according to the invention of a zeolite deposited on a silicon carbide support results, on the contrary, in the maintenance of a substantially constant catalytic activity over very long periods of time, typically for at least 20 hours or even much longer.

The stabilisation obtained within the scope of the present invention appears to be explained, inter alia, by the very good thermal conductivity of the silicon carbide support that is used, which allows the heat formed during the conversion reaction of methanol to dimethyl ether to be dissipated very quickly, thus avoiding the formation of hot spots within the catalytic bed, which reduces especially the risks of poisoning of the catalyst by coking.

Moreover, the SiC-supported zeolites used according to the present invention have a particularly high catalytic activity in the conversion reaction of methanol to dimethyl ether, which is found in most cases to be at least comparable with that of conventional commercial catalysts. Accordingly, the benefit obtained in terms of stability is generally not at the expense of the effectiveness of the catalyst. In other words, the improvement brought about within the scope of the invention contributes effectively to an overall improvement in the catalytic properties.

In addition, the use of zeolites in a form supported on a silicon carbide support results in very small losses of potential, which are in any case much smaller than in the case of the use of non-supported zeolites.

Another advantage of the catalysts used according to the invention is that the immobilisation of the zeolites on a silicon carbide support brings about an improvement in the mass and heat transfers in the reactor in which the conversion reaction of methanol to dimethyl ether is carried out.

Moreover, it is to be noted that the SiC support used according to the invention is a rigid support, which therefore confers to the catalyst good mechanical stability. Furthermore, SiC is a chemically inert material which is therefore not liable to cause parasitic reactions during the conversion reaction of methanol to dimethyl ether.

These various advantages make the process of the present invention a very interesting alternative to the methods of converting methanol into dimethyl ether which are known at present, especially since the use of the supported catalyst of the invention further permits the use of crude methanol having a high water content (for example comprising from 20 to 40% by volume water), such as methanol obtained from biomass, which is at present under consideration as a raw material for the large-scale production of dimethyl ether as an alternative fuel.

As the zeolite-based catalyst which can be used within the scope of the present invention, the catalysts for the alkylation and acylation of aromatic compounds described in patent application WO 03/59509 can especially be employed.

More generally, the catalyst used according to the invention can especially be synthesised by carrying out the zeolite deposition on an SiC support by the hydrothermal method according to techniques known per se, especially of the type described in the above-mentioned application WO 03/59509.

According to an advantageous preparation method, the catalyst used according to the invention is a catalyst which is synthesised by carrying out the following steps:

(A) a heat treatment ("calcination treatment") of the SiC support, this treatment generally being carried out at a temperature of from 800 to 1000° C. (typically at a temperature of the order of 900° C.) for several hours (most frequently of the order of from 2 to 6 hours), which results in the formation of a superficial layer of silica on the surface of the support.

In fact, the heat treatment so carried out is a support pretreatment step which induces a conversion of the surface silicon carbide and silicon oxycarbide species to the form of silica. The resulting silica layer serves as the anchoring point for the subsequent deposition of the zeolite on the support.

Especially so as to ensure effective anchoring between the support and the deposited zeolite, it is preferable for the silica layer obtained on the surface of the support following the calcination to have a thickness of at least 1 nm and more preferably of at least 2 nm. However, it is preferable for the thickness of the silica layer produced to remain sufficiently small: if it is too thick, it tends to dissolve when the zeolite is subsequently deposited. In addition, the deposition of a sufficiently thin layer of zeolite allows the accessibility of the methanol at the reactive sites and the removal of the dimethyl ether that is formed to be optimised. In general, it is interesting for the layer formed to have a thickness less than or equal to 10 nm. Advantageously, the layer of silica formed has a thickness of from 1.5 to 5 nm. The thickness of the layer of silica formed can be determined especially by XPS ("X-ray photoelectron spectroscopy").

(B) the incorporation of the modified support obtained in the preceding step into the synthesis medium of a zeolite, whereby the zeolite gradually becomes anchored to the support during its formation.

Within this context, it is preferable to introduce the modified support obtained in step (A) into a gelled medium (gel) as obtained in the preparation of a zeolite by the hydrothermal method. In that case, the addition of the support to the zeolite synthesis medium is preferably carried out immediately before, during or immediately after maturing of the synthesis medium. Typically, the modified support obtained in step (A) is added to the gel before or during the maturing, and the mixture obtained following maturing is transferred to a vessel suitable for syntheses by the hydrothermal method, for example to a Teflon-lined autoclave. Within this context, the method described in the article by B. Louis et al. in Applied Catalysis A210, p. 103 (2001) can advantageously be used.

It is to be emphasised that step (B) can optionally be repeated in order to carry out the successive deposition of a plurality of zeolite layers, the number of depositions carried out especially allowing the thickness of the deposited layer to be adjusted.

Whatever the method of preparing the catalyst used according to the invention, the SiC support used to form it preferably has a specific surface area that is as high as possible, especially in order to ensure that the zeolite is anchored as effectively as possible to the support. Within this context there is used a silicon carbide support having a specific surface area of preferably greater than 2 $m^2/g$, more preferably of at least 5 $m^2/g$, more advantageously of at least 10 $m^2/g$, or even of at least 20 $m^2/g$, the specific surface area generally remaining below 600 $m^2/g$, in most cases below 400 $m^2/g$ and typically below 200 $m^2/g$, or even below 100 $m^2/g$. According to a particularly suitable embodiment of the invention, the specific surface area of the silicon carbide support is from 2 to 40 $m^2/g$, typically from 5 to 25 $m^2/g$. Within the context of the present description, the term "specific surface area" refers to the specific BET surface area, as determined by nitrogen adsorption, according to the known so-called BRUNAUER-EMMET-TELLER method which is described in *The journal of the American Chemical Society*, Volume 60, page 309 (1938) and corresponding to international standard ISO 5794/1 (annex D).

According to an interesting embodiment, the silicon carbide of the support used according to the invention is constituted of a silicon carbide of beta structure (called "β-SiC") or alternatively it at least comprises silicon carbide of beta structure in an amount of at least 80% by mass, or even at least 90% by mass, based on the total mass of the support. Among other advantages, silicon carbides of type β-SiC have the advantage of having a particular porosity, which substantially comprises macropores and mesopores, with pore sizes typically ranging from 4 to 100 nm. That porosity is additionally substantially free of micropores, which would be liable to cause problems of diffusion of the reagents and the reaction products. Within the context of the present description, "micropores" are understood as being pores having a size less than 2 nm, "macropores" denoting pores having sizes greater than 50 nm and "mesopores" denoting pores of intermediate size, ranging from 2 to 50 nm. The specific porosity of silicon carbides of type β-SiC permits very good accessibility of the methanol at the catalytic sites as well as excellent properties of removal of the products formed. These optimised exchanges between catalyst and external medium manifest themselves especially in an increased yield for the conversion reaction of methanol to dimethyl ether. In addition, it seems possible that these optimised exchanges allow the phenomena of poisoning of the catalyst by coking (phenomenon of deposition of carbon on the catalyst due to secondary reactions) to be prevented. A type β-SiC silicon carbide support of the above-mentioned type can be obtained especially by gas/solid reaction between gaseous SiO and solid carbon. Within this context, the reaction is generally carried out using SiO vapours generated in situ in the reactor or in the matrix of a precursor solid. An advantage of β-SiC-based supports is that their synthesis generally yields macroscopic materials, directly, without the need for an additional forming step. Accordingly, within the scope of the present invention, a β-SiC-based support as obtained directly after its synthesis can be used for carrying out a deposition of zeolite thereon. According to another embodiment, the β-SiC-based support is subjected to heat pretreatment following its synthesis, typically at a temperature of 900° C., where appropriate preferably for at least one hour.

According to a possible embodiment, the silicon carbide of the support used according to the invention can comprise a silicon carbide of alpha structure (called "α-SiC"), which has been found to be valuable especially in terms of the mechanical strength properties of the catalyst. In that case, the support advantageously comprises the silicon of alpha structure (α-SiC) in admixture with silicon carbide of beta structure (β-SiC), which allows the advantages of both types of silicon carbide to be used. Within this context, it is generally preferred to use SiC supports wherein the mass ratio α-SiC/β-SiC is from 1:99 to 50:50, for example from 5:95 to 20:80. In general, a support according to the invention comprising silicon carbide of alpha structure is obtained by compacting a powder comprising particles of α-SiC and one or more binders.

The SiC support of the catalysts used according to the invention can be employed in different forms.

Thus, according to a possible embodiment, the SiC support can be in the form of macroscopic objects of the grain, extrudate, rod, monolith or tube type typically having a specific surface area of from 2 to 50 $m^2/g$, in most cases from 5 to 30 $m^2/g$. Within this context it is possible, for example, to use SiC supports of the type obtained according to the methods described in documents EP 0 313 480, EP 0 440 569, U.S. Pat. No. 5,217,930, EP 0 511 929 or EP 0 543 751, which allow materials of various sizes and forms to be obtained.

According to another particularly advantageous embodiment of the invention, the SiC support used has an open macroscopic structure. Within this context, the SiC support preferably has a rigid cellular foam structure, the support then preferably having a specific surface area of from 2 to 400 $m^2/g$, the specific surface area in most cases being from 5 to 50 $m^2/g$, advantageously greater than 10 $m^2/g$ and preferably greater than 20 $m^2/g$, more advantageously greater than 30 $m^2/g$. An SiC support in the form of a rigid cellular foam used according to the invention preferably comprises at least 80% by mass β-SiC, or even at least 90% by mass β-SiC, based on the total mass of the catalyst. According to an interesting embodiment of the invention there is used a support which is a rigid cellular foam constituted substantially of β-SiC (most frequently comprising β-SiC in an amount of at least 95% by mass, or even 99% by mass or more, based on the total mass of the support).

The specific surface area of an SiC support of open macroscopic structure such as a rigid cellular foam used according to the invention is typically from 2 to 100 $m^2/g$, most frequently from 5 to 50 $m^2/g$. SiC cellular foams of that type can be obtained especially by the process described in documents EP 543 752, U.S. Pat. No. 5,449,654 or U.S. Pat. No. 6,251,819. Rigid cellular foams of β-SiC that are particularly suitable according to the invention preferably have pore sizes of from 300 to 5000 microns, advantageously from 1000 to 4000 microns, especially from 2000 to 3500 microns. The open porosity (macroporosity) of the rigid cellular foam can vary from 30 to 90%, preferably from 35 to 80%, especially from 40 to 70% by volume, based on the total volume of the material.

The use of an SiC support having a rigid cellular foam structure instead of a more compact support results in an even more marked improvement in the stability of the catalyst as well as a significant improvement in the activity of the catalyst for the conversion reaction of methanol to dimethyl ether.

Moreover, the works by the inventors have also demonstrated that the use of alveoloar foam type supports of the above-mentioned type induces losses of potential that are much more limited than in the case of more compact materials.

In particular, the very open porous structure of the rigid cellular SiC foams allows the problems of loss of potential through the catalytic bed to be reduced considerably. More precisely, the cellular structure permits the use of much higher space velocities of reagents (in gas form) without experiencing an excessive loss of potential through the catalytic bed.

It is also to be noted that the use of a support of the rigid cellular foam type permits good diffusion of the methanol to the active catalytic sites (which are found at the surface or partly within the pores of the catalyst) and the removal of the dimethyl ether produced outside the catalytic zone, even with the use of the high reagent flow rates which are generally required to achieve optimised productivity of the conversion process. These effects are particularly interesting in the case of consecutive reactions as are carried out in the process of the invention. This phenomenon is especially explained by the fact that the thickness of the solid walls of the rigid foam is relatively thin as compared with that of a grain or an extrudate, that small thickness permitting better diffusion of the various species, particularly when the zeolite is deposited on the support in the form of a sufficiently thin layer.

In addition, supports with open porosity of the rigid cellular foam type exhibit a connected structure which confers on them good heat conduction properties which are improved as compared with the use of a more compact support such as a support in the form of grains, which are used stacked one against the other inside the reactor with less effective grain-grain contact. In the case of the use of an SiC support having a rigid cellular foam structure, the transfer of heat is of two orders, namely:

(i) local heat transfer, from the catalytic site (the zeolite deposited on said support) to the SiC support, and
(ii) overall heat transfer, over the totality of the foam interconnected by connected rigid bridges.

The existence of that overall heat transfer, linked to the structure of the support of open porosity that is used, is found particularly for permitting dissipation of the pronounced heat of reaction liberated by the catalysed reaction, particularly when high reagent velocities are being used in order to increase productivity.

Owing to their specific structure, supports with open porosity of the rigid cellular foam type allow the phenomena of catalyst deactivation observed with the catalysts known at present to be reduced significantly, particularly when the zeolite is deposited on the support in the form of a layer of small thickness, advantageously less than 10 nm and more preferably less than 5 nm.

Supports with open porosity of the rigid cellular foam type additionally have not inconsiderable mechanical strength, making it possible to load the reactor in a manner different from that used with catalysts in grain or extrudate form. In particular, it is possible to use the supports in the form of macroscopic materials of large dimensions which are able to fit the inside volume of the catalyst, typically foams in the form of cylinders having a diameter equal to (or slightly less than) the inside diameter of a cylindrical reactor, or alternatively in the form of materials which can be stacked or juxtaposed in order to occupy the inside volume of reactors of large size.

Whatever the precise nature of the SiC support used according to the invention, the zeolite which is immobilised (generally deposited) on the support is preferably substantially in its catalytically active form. Accordingly, in the case of a zeolite of type ZSM-5, it is preferred for the substantial part of the zeolite deposited on the SiC support to be in its acidic (protonated) form: H-ZSM-5. To this end, the catalyst can, if required, be activated prior to the reaction by known methods, for example by treating the zeolite with an ammonium salt (for example ammonium chloride) then subjecting the resulting zeolite to heat treatment in order to remove the ammonia-containing species.

In addition, especially in order to facilitate the diffusion of the reagents and of the products in the region of the catalyst and also to facilitate local heat exchanges between the active catalytic sites and the SiC support, it is most frequently preferable for the zeolite immobilised on the SiC support to be in the form of a deposited layer of relatively small thickness, that layer preferably having an average thickness of less than 50 microns, more preferably less than 20 microns and yet more advantageously less than 10 microns. In order to retain sufficient catalytic activity, however, it is preferable for the average thickness to be at least 1 micron, more preferably at least 3 microns. Average thicknesses that are highly suitable according to the invention are, for example, of the order of from 5 to 10 microns. The average thickness of the zeolite layer to which reference is made here can be determined by scanning electron microscopy on ground sections of specimens.

The specific use of the catalyst of the invention allows the catalytic dehydration reaction of methanol to dimethyl ether to be conducted within a wide temperature range without any loss of activity of the catalyst, which constitutes yet another advantage of the catalysts used according to the invention. Most frequently, it is preferable to conduct the reaction at a temperature of from 200 to 500° C., preferably at temperatures below 400° C., for example from 220 to 350° C., especially from 250 to 300° C.

In addition, with the supported catalysts used according to the invention, the catalytic dehydration reaction of methanol to dimethyl ether does not have to be carried out under pressure. It can accordingly be carried out under atmospheric pressure, which is reflected in the ease of use of the process and in reduced costs. More generally, the catalytic dehydration reaction of methanol to dimethyl ether can be carried out under pressures greater than or equal to atmospheric pressure, in particular at average pressures generally used in methanol production units or as a function of post-reaction needs and also for reasons associated with the productivity of the process. The process can accordingly be conducted at pressures ranging from 1 to 50 bar, for example at pressures of from 2 to 40 bar, in particular from 5 to 30 bar.

Within the scope of the present invention, the catalytic dehydration reaction of methanol can typically be carried out with an hourly space velocity of from 1 to 20 h$^{-1}$, for example from 1 to 5 h$^{-1}$, NTP.

The process of the invention enables the reaction for converting methanol into dimethyl ether to be carried out very easily, with rates of conversion which are generally high and which, especially, remain stable over time.

In addition, in the process of the invention, the methanol used in the catalytic dehydration reaction does not have to be purified. It can accordingly contain a certain number of impurities or additional compounds (such as water, for example), with the proviso, of course, that those impurities are not of a nature such as to affect the stability of the catalyst or result in secondary reactions which are undesirable within the scope of the intended application.

Thus, according to an embodiment of the invention suitable for the synthesis of relatively pure dimethyl ether, it is possible to employ in the dehydration reaction a methanol that is substantially free of impurities.

According to another embodiment suitable for carrying out the invention, it is also possible to use a crude methanol in the dehydration reaction (for example crude methanol obtained from biomass) or alternatively, more generally, a medium comprising methanol in admixture with other compounds and/or impurities, that crude methanol or methanol-based medium then most frequently comprising from 10 to 90% by mass methanol. Within this context, it is most frequently found to be advantageous for the methanol content to be at least 20% and more preferably at least 30% by mass.

BRIEF DESCRIPTION OF THE DRAWINGS

Various aspects and advantages of the process of the invention will become more explicitly apparent from the examples below, which are given with reference to the accompanying figures, wherein.

EXAMPLE 1

Preparation of a ZSM-5 Zeolite Supported on SiC Extrudates

Catalyst C1

In this example, a catalyst C1 was prepared by depositing a zeolite layer on a β-SiC support from a precursor gel by the hydrothermal method. More precisely, the following steps were carried out:

1.1 Pretreatment of the SiC Support

In this example, β-SiC extrudates of cylindrical shape having a length of 5 mm and a diameter of 2 mm were used as the support. The specific BET surface area of the β-SiC extrudates is 5 m$^2$/g.

The β-SiC extrudates were calcined in the air at 900° C. for 5 hours so as to form on their surface a silica layer having a thickness of from 5 to 10 nm.

1.2 Preparation of a Zeolite Precursor Gel 200 ml of distilled water were poured, at ambient temperature (25° C.), into a 500 ml beaker, and 2.23 g of sodium chloride were then added thereto.

With vigorous stirring, 0.123 g of anhydrous sodium aluminate (NaAlO$_2$) was introduced, followed by 24 ml of tetrapropylammonium hydroxide (TPAOH, of formula $^+$N(C$_3$H$_7$)$_4$.OH$^-$, which served as organic structuring agent).

With continued stirring, 14 ml of tetraethoxysilane (TEOS, of formula Si(OC$_2$H$_5$)$_4$) were introduced. This addition was divided into seven additions of 2 ml each, the mixture being stirred for several minutes between each addition in order to ensure that the TEOS dissolved completely.

There was thus obtained an aqueous gel having the following molar composition:
TPAOH:TEOS:NaCl:NaAlOH:H$_2$O=2.16:5.62:3.43: 0.13:1000

1.3 Addition of SiC and Maturing of the Medium

The heat treated β-SiC obtained following step 1.1 was introduced into the gel obtained in step 1.2.

The medium so obtained was allowed to mature by being stirred at ambient temperature (25° C.) for 4 hours.

1.4 Formation of the Zeolite on the β-SiC Support

After maturing, the medium was transferred to a Teflon-lined autoclave, which was placed in an oven at 170° C. for 48 hours.

The synthesis of the zeolite so effected was conducted under autogenic conditions.

After the 48 hours of heat treatment, the autoclave was cooled and the solid present in the medium was recovered. The solid is then rinsed by filtration and then washed with copious amounts of distilled water, followed by sonication for 30 minutes and finally drying in an oven.

The resulting solid was then subjected to heat treatment at 500° C. for 5 hours in order to remove the organic structuring agent.

1.5 Deposition of a Second Layer of Zeolite

The material as obtained following step 1.4 was introduced into a gel as obtained in step 1.2, which was stirred.

The medium so obtained was allowed to mature by being stirred at ambient temperature (25° C.) for 4 hours.

After maturing, the medium was transferred to a Teflon-lined autoclave, which was placed in an oven at 170° C. for 60 hours (autogenic conditions).

After the 60 hours of synthesis, the autoclave was cooled and the solid present in the medium was recovered. The solid is then rinsed by filtration and then washed with copious amounts of distilled water and finally dried in an oven. The resulting solid was then treated for 5 hours at 500° C. in order to remove the organic structuring agent.

1.6 Formation of the Final Form of the Catalyst ("Activation")

The solid material as obtained following step 1.5 was introduced into a solution is brought into contact with a 1M $NH_4Cl$ solution and the mixture was refluxed for 16 hours.

The ammonium form of the zeolite was thus obtained.

Following that treatment, the solid present in the medium was filtered off, washed with copious amounts of distilled water and then dried and finally calcined at 550° C. for 5 hours. The latter heat treatment results in the removal of the ammonia, which yields the acid form of the zeolite.

Catalyst C1 (in which the zeolite is in its H-ZSM-5 form) was thus obtained.

By means of X-ray diffraction it was verified that the catalyst C1 obtained exhibits diffraction bands characteristic of H-ZSM-5 zeolite, namely bands characteristic of the MFI crystal structure. Indexing of this peak was carried out in accordance with the JCPDS (Joint Committee on Powder Diffraction Standards) database. These bands were also observed for the solid obtained following step 1.4, but with a relatively low intensity, which indicates that step 1.5 has effectively increased the amount of zeolite deposited on the support.

In addition, electron microscope photographs indicate that the entire surface of the SiC support is covered homogeneously by crystals of zeolite ZSM-5, which are substantially hexagonal crystals having a size greater than 4 microns. This homogeneous covering of the support does not affect the initial morphology of the support.

The specific surface area determined by nitrogen adsorption of the catalyst C1 obtained is 55 $m^2/g$, that is to say a surface area eleven times greater than that of the extrudates alone.

EXAMPLE 2

Preparation of a ZSM-5 Zeolite Supported on a SiC Foam

Catalyst C2

In this example, a catalyst C2 was prepared by depositing a zeolite on a β-SiC support from a precursor gel, according to the hydrothermal method, under the same conditions as in steps 1.2 to 1.5 of Example 1 but replacing the extrudates used in Example 1 by a β-SiC cellular foam having a specific BET surface area of 19 $m^2/g$ and having the following characteristics: cellular foams obtained by the method described in FR2860992 having a pore size of 1750 microns, a diameter of 25 mm and a length of 4 cm.

Like the extrudates of Example 1, the β-SiC foam used in the present Example 2 was calcined beforehand in the air at 900° C. for 5 hours in order to form a layer of silica on its surface.

A precursor gel was then prepared under the conditions of step 1.2 of Example 1, and the pretreated β-SiC foam was added to the gel before the medium was left to mature. The zeolite was then formed on the support under the conditions of step 1.4 of Example 1, and then a second layer of zeolite was deposited, the two layers subsequently being brought into the acidic form under the conditions of steps 1.5 and 1.6, respectively, of Example 1.

Following these various steps, the catalyst C2 was obtained.

Figure 4:
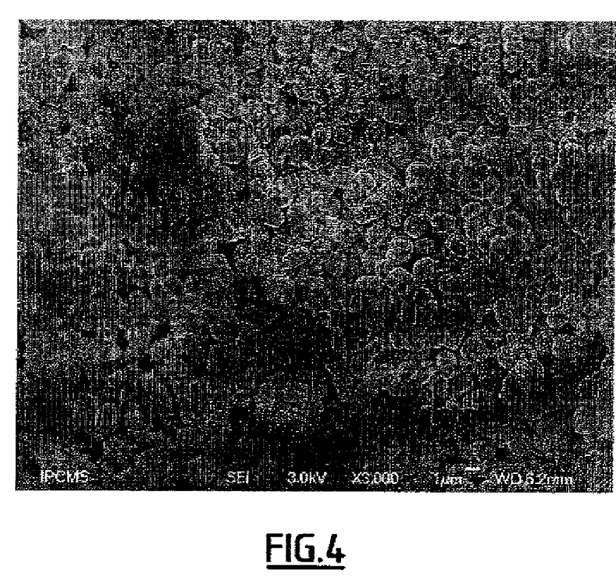
FIG. 4 is a transmission electron microscope photograph of the catalyst C2 used in the examples.

In this case too, analyses by electron microscopy show that the entire surface of the β-SiC support is covered homogeneously with crystals of zeolite ZSM-5, which are substantially hexagonal crystals less than 4 microns in size. The homogeneous covering of the support does not affect the initial morphology of the support, as is shown in the accompanying FIG. 4.

This time too, the deposition of zeolite on the cellular foam support allowed a high specific surface area to be obtained, namely of 120 $m^2/g$, that is to say a surface area 6 times greater than that of the foam on its own.

EXAMPLE 3

Synthesis of Dimethyl Ether Using Catalysts C1 and C2

Each of the catalysts C1 and C2 prepared in Examples 1 and 2 was used to catalyse the conversion reaction of methanol to dimethyl ether.

In all cases, the conversion reaction was conducted under atmospheric pressure, at a temperature of 400° C.

The methanol was introduced with the aid of an HPLC pump, at a flow rate of 0.5 ml/min, into an argon flow (Argon 4.5 marketed by Air Liquide) where it is vaporised and guided to a reactor containing the catalyst. The flow rate of the argon flow is 80 cc/min.

The reactor used is constituted of a quartz tube which has an inside diameter of 1 inch (25.4 mm) and is equipped with a frit on which 4 g of the catalyst in question have been deposited. The reactor is placed in an oven heated to 400° C.

The temperature was controlled with the aid of two thermocouples, one being placed in the oven outside the reactor in order to regulate the temperature of the oven and the other being placed inside the catalytic bed. In addition, all the lines downstream of the reactor were heated with the aid of heating wire which maintained them at 100° C., in order to avoid condensation of the reaction products.

The products which formed were analysed by gas phase chromatography in the case of the gaseous products and by liquid phase chromatography in the case of the liquid products, with the aid of a Varian CP 3800 chromatograph equipped with a DB-1 capillary column (length: 30 m-inside diameter: 0.53 mm) and an FID detector (flame ionisation detector). Acquisition of the data was carried out in an automated manner with the aid of the software supplied by Varian, allowing the temperature program to be controlled and the signal sent by the detector to be processed (integration of the peaks).

For comparison purposes, the reaction was conducted under the same conditions with two other control catalysts, namely:

T1: non-supported ZSM-5 zeolite, prepared under the conditions of step 1.4 of Example 1 but without the prior addition of β-SiC support T2: commercial catalyst Zeolyst (CBV 8014) (type MFI zeolite characterised by a Si/Al ratio of 40)

Figure 1:
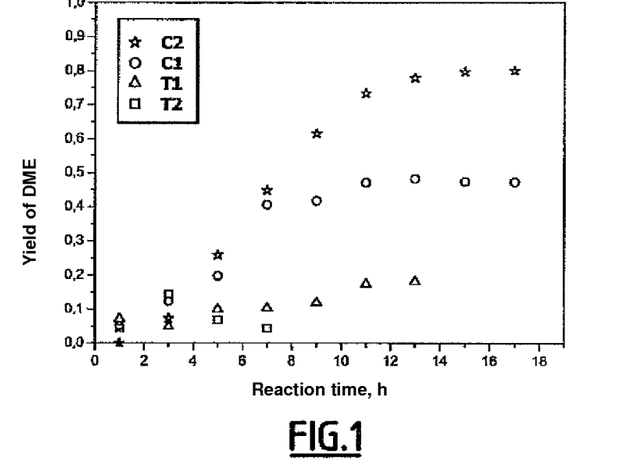
FIG. 1 shows the evolution of the conversion reaction of methanol to dimethyl ether under the conditions of Example 3.

The accompanying FIG. 1 shows the evolution of the yield of dimethyl ether over time with the four catalysts tested.

With catalysts C1 and C2 according to the invention, the yield stabilises rapidly and remains substantially constant until the end of the 17 hours of reaction.

For catalyst C1, the yield remains above 50% once it has stabilised, throughout the reaction.

Even more interesting results are obtained for catalyst C2, where the conversion and yield of DME remain stable between 80 and 90% after stabilisation, throughout the reaction. The improvement observed over catalyst C1 is probably explained at least partly by the increased ability of the cellular foam structure to dissipate the heat of reaction.

Conversely, with the controls T1 and T2, a drastic loss of activity is observed as early as the first few hours of the reaction.

The results obtained in respect of selectivity show that there is no formation of saturated hydrocarbons resulting from the deactivation of the catalyst, which confirms the remarkable stability of the catalysts according to the invention, in particular that of the catalyst C2, which permits the conversion of 84% of the methanol introduced into the reactor, converting 95% of it into dimethyl ether.

EXAMPLE 4

Synthesis of Dimethyl Ether Using Catalyst C2

Catalyst C2 prepared in Example 2 was used to catalyse the conversion reaction of methanol to dimethyl ether under conditions relatively similar to those of Example 3, namely under atmospheric pressure but this time at a temperature of 270° C.

The methanol was introduced with the aid of an HPLC pump, using two flow rates 0.6 and 1.4 ml/min, into an argon flow (Argon 4.5 marketed by Air Liquide) where it is vaporised and guided to a reactor containing the catalyst. Two values for the argon flow were taken during the test: 80 and 160 ml/min.

The reactor used is constituted of a quartz tube which has an inside diameter of 1 inch (25.4 mm) and is equipped with a frit on which 4 g of the catalyst in question have been deposited. The reactor is placed in an oven heated to 270° C.

The temperature was controlled with the aid of two thermocouples, one being placed in the oven outside the reactor in order to regulate the temperature of the oven and the other being placed inside the catalytic bed. In addition, all the lines downstream of the reactor were heated with the aid of heating wire which maintained them at 100° C., in order to avoid condensation of the reaction products.

The products which formed were analysed by gas phase chromatography in the case of the gaseous products and by liquid phase chromatography in the case of the liquid products, with the aid of a Varian CP 3800 chromatograph equipped with a DB-1 capillary column (length: 30 m-inside diameter: 0.53 mm) and an FID detector (flame ionisation detector). Acquisition of the data was carried out in an automated manner with the aid of the software supplied by Varian, allowing the temperature program to be controlled and the signal sent by the detector to be processed (integration of the peaks).

Figure 2:
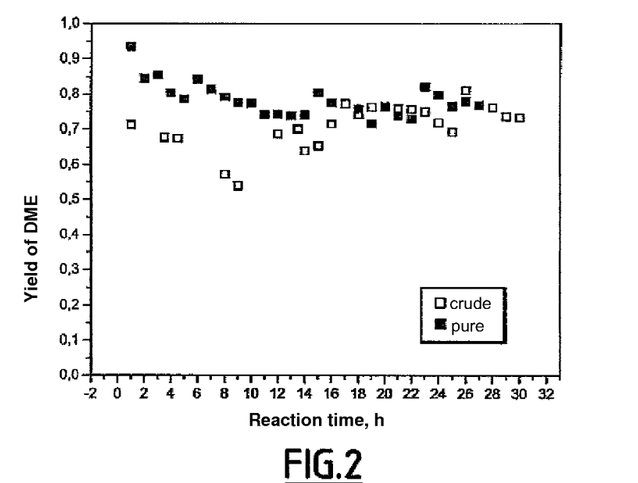
FIG. 2 shows the evolution of the conversion reaction of methanol to dimethyl ether under the conditions of Example 4.

The accompanying FIG. 2 shows the evolution of the yield of DME as a function of time and the reaction conditions.

The increase in the quantity of methanol does not change the behaviour of the catalyst, and the yield of DME remains stable at around 0.8.

EXAMPLE 5

Synthesis of Dimethyl Ether Using Catalyst C2

Catalyst C2 prepared in Example 2 was used to catalyse the conversion reaction of methanol to dimethyl ether under conditions relatively similar to those of Example 3, namely under atmospheric pressure but this time at a temperature of 270° C.

The methanol was introduced with the aid of an HPLC pump, using a single flow rate of 0.6, into an argon flow (Argon 4.5 marketed by Air Liquide) where it is vaporised and guided to a reactor containing the catalyst. One value for the argon flow was taken during the test: 80 ml/min.

The reactor used is constituted of a quartz tube which has an inside diameter of 1 inch (25.4 mm) and is equipped with a frit on which 4 g of the catalyst in question have been deposited. The reactor is placed in an oven heated to 270° C.

The temperature was controlled with the aid of two thermocouples, one being placed in the oven outside the reactor in order to regulate the temperature of the oven and the other being placed inside the catalytic bed. In addition, all the lines downstream of the reactor were heated with the aid of heating wire which maintained them at 100° C., in order to avoid condensation of the reaction products.

The products which formed were analysed by gas phase chromatography in the case of the gaseous products and by liquid phase chromatography in the case of the liquid products, with the aid of a Varian CP 3800 chromatograph equipped with a DB-1 capillary column (length: 30 m-inside diameter: 0.53 mm) and an FID detector (flame ionisation detector). Acquisition of the data was carried out in an automated manner with the aid of the software supplied by Varian, allowing the temperature program to be controlled and the signal sent by the detector to be processed (integration of the peaks).

Catalyst C2 was tested with pure methanol and, for comparison purposes, with crude methanol, namely a mixture $CH_3OH/H_2O=80/20$ vol. %.

Figure 3:
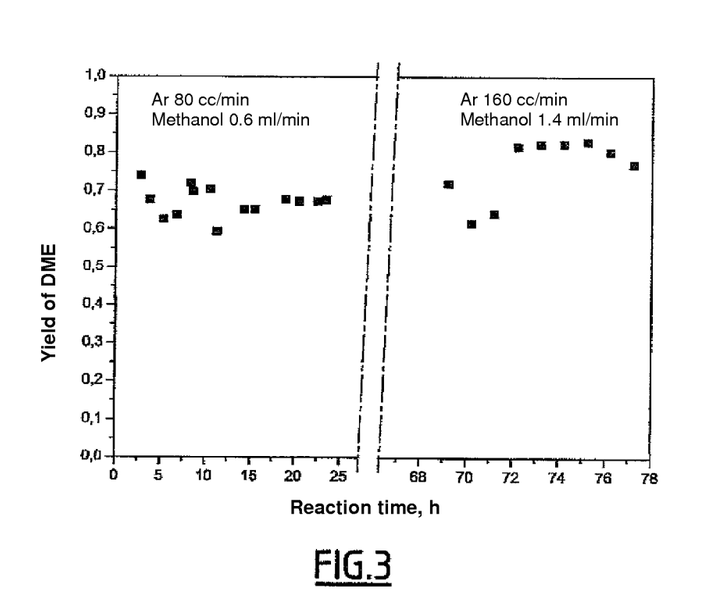
FIG. 3 shows the evolution of the conversion reaction of methanol to dimethyl ether under the conditions of Example 5.

The accompanying FIG. 3 shows the evolution of the yield of dimethyl ether over time.

At the start, the composite exhibits a better yield in the reaction with pure methanol of about 0.8. In the reaction with crude methanol, the composite has a lower conversion but better selectivity, and at the end of 18 hours the yield is identical for the two reactions.

The invention claimed is:

1. A process for preparing dimethyl ether, comprising:
   providing a catalyst comprising a zeolite immobilised on a silicon carbide support, the support comprising a rigid cellular foam; and
   catalytically dehydrating methanol utilizing the catalyst.

2. The process of claim 1, wherein the silicon carbide support has a specific surface area greater than 2 $m^2/g$.

3. The process of claim 1, wherein the zeolite is an MFI-type zeolite.

4. The process of claim 1, wherein the zeolite is based on an aluminosilicate having a molar ratio Si/Al of from 20 to 100.

5. The process of claim 1, wherein the zeolite is a ZSM-5 zeolite.

6. The process of claim 1, wherein the silicon carbide support comprises silicon carbide of beta structure (β-SiC) in an amount of at least 80% by mass, based on total mass of the support.

7. The process of claim 1, wherein the silicon carbide support comprises a mixture of silicon carbide of alpha structure (α-SiC) in admixture with silicon carbide of beta structure (β-SiC).

8. The process according to claim 7, wherein the mass ratio α-SiC/β-SiC is from 1:99 to 50:50.

9. The process of claim 1, wherein the rigid cellular foam has pore sizes of from 300 to 5000 microns.

10. The process of claim 1, wherein the rigid cellular foam comprises β-SiC.

11. The process of claim 1, wherein the silicon carbide support has a specific surface area of from 5 to 50 m$^2$/g.

12. The process of claim 1, wherein the zeolite is in a form of a layer having an average thickness of from 1 to 50 microns.

13. The process of claim 1, wherein the catalytic dehydration of methanol is conducted at a temperature of from 200° C. to 500° C.

14. The process of claim 1, wherein the catalytic dehydration of methanol is conducted at a temperature of from 220° C. to 350° C.

15. The process of claim 1, wherein the catalytic dehydration of methanol is carried out under a pressure of from 1 to 50 bar.

16. The process of claim 1, wherein the catalytic dehydration of methanol is carried out under atmospheric pressure.

17. The process of claim 1, wherein the catalytic dehydration of methanol is carried out with an hourly space velocity of from 1 to 20 h$^{-1}$ NTP.

18. The process of claim 1, wherein the methanol used in the catalytic dehydration is substantially free of impurities.

19. The process of claim 1, wherein the methanol used in the catalytic dehydration comprises methanol in admixture with other compounds and/or impurities.

* * * * *